(12) United States Patent
Okamoto

(10) Patent No.: US 6,420,582 B1
(45) Date of Patent: Jul. 16, 2002

(54) ORGANOMETALLIC COMPOUNDS FOR CHEMICAL VAPOR DEPOSITION AND THEIR PREPARING PROCESSES, AND PROCESSES FOR CHEMICAL VAPOR DEPOSITION OF PRECIOUS-METAL FILMS AND PRECIOUS-METAL COMPOUND FILMS

(75) Inventor: Koji Okamoto, Kanagawa (JP)

(73) Assignee: Tanaka Kikinzoku Kogyo K.K., Tokyo (JP)

( * ) Notice: Subject to any disclaimer, the term of this patent is extended or adjusted under 35 U.S.C. 154(b) by 0 days.

(21) Appl. No.: 09/960,510

(22) Filed: Sep. 24, 2001

(30) Foreign Application Priority Data

Oct. 11, 2000 (JP) ......................................... 2000-310503

(51) Int. Cl.[7] ........................ C07F 17/02; C23C 16/00; C23C 14/26
(52) U.S. Cl. .................... 556/136; 427/248.1; 427/587; 427/593
(58) Field of Search ....................... 556/136; 427/248.1, 427/587, 593

(56) References Cited

U.S. PATENT DOCUMENTS

| | | | | | |
|---|---|---|---|---|---|
| 4,992,305 | A | * | 2/1991 | Erbil | ........................... 427/226 |
| 6,002,036 | A | * | 12/1999 | Kodokura | ................. 427/248.1 |
| 6,207,232 | B1 | * | 3/2001 | Kadokura | .................... 427/252 |

* cited by examiner

Primary Examiner—Porfirio Nazario-Gonzalez
(74) Attorney, Agent, or Firm—Arent Fox Kintner Plotkin & Kahn, PLLC

(57) ABSTRACT

A first organometallic compound is an organometallic compound for manufacturing a ruthenium film or a ruthenium compound film by a chemical vapor deposition process, wherein the organometallic compound is alkylcyclopentadienyl(cyclopentadienyl)ruthenium having a substituent of n-propyl group, iso-propyl group, n-butyl group, iso-butyl group, tert-butyl group. A second organometallic compound is an organometallic compound for manufacturing an iridium film or an iridium oxide film by a chemical vapor deposition process, wherein the organometallic compound for chemical vapor deposition is alkylcyclopentadienyl(1,5-cyclooctadiene)iridium having a substituent of any alkyl group of n-propyl group, iso-propyl group, or n-butyl group, iso-butyl group, tert-butyl group.

6 Claims, No Drawings

ORGANOMETALLIC COMPOUNDS FOR CHEMICAL VAPOR DEPOSITION AND THEIR PREPARING PROCESSES, AND PROCESSES FOR CHEMICAL VAPOR DEPOSITION OF PRECIOUS-METAL FILMS AND PRECIOUS-METAL COMPOUND FILMS

BACKGROUND OF THE INVENTION

1. Field of the Invention

The present invention relates to organometallic compounds for manufacturing precious-metal films or precious-metal compound films by a chemical vapor deposition process. In particular, the present invention relates to organometallic compounds for manufacturing films of ruthenium and iridium, as a precious-metal, and their compounds. In addition, it relates to a process for manufacturing precious-metal films or precious-metal compound films using these organometallic compounds.

2. Description of the Related Art

Recently, there is a continuing need for higher performance of semiconductor devices, and for DRAMs (dynamic RAMs), researches are made with the aim of increasing their capacity from Mbit to Gbit sizes. Following this trend, technologies for densification and high integration of semiconductor devices are rapidly advanced, and in order to increase their capacity, attempts are made to improve not only their structure, but also materials used for these devices.

Under these circumstances, materials that receive recent attention as film electrode materials for DRAMs are precious metals or precious-metal oxides, and among them, ruthenium or iridium or oxides thereof. The reason is that these materials have a low resistivity, and possess superior electric properties when electrodes are produced. Consequently, these materials receive attention as becoming one of important materials for film electrodes in the future. Specifically, in the above-described DRAMs, these are examined, for example, for uses as materials for accumulating electrodes of capacitors, and are believed to be able to make a major contribution to their densification.

As a method for manufacturing precious-metal or a precious-metal film is utilized a chemical vapor deposition process (hereinafter, referred to as a CVD process) in general. This is due to, according to a CVD process, easy manufacturing of uniform films, and at the same time superiority in step coverage (ability to cover differences in level). Additionally, it is likely that a CVD process will be the mainstream of coming processes for manufacturing film electrodes which can be adapted to densify recent circuits and electronic components to a higher extent.

With respect to ruthenium, as a raw material for ruthenium films and ruthenium compound films, investigations have been recently conducted on use of bis(ethylcyclopentadienyl)ruthenium shown by the following formula. This bis(ethylcyclopentadienyl)ruthenium is a compound in which one hydrogen on each of two cyclopentadiene rings in bis(cyclopentadienyl)ruthenium (commonly called ruthenocene) is substituted with an ethyl group.

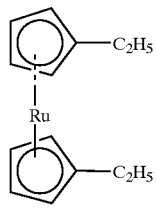

(Formula 1)

On the other hand, as a raw material for iridium films, ethylcyclopentadienyl(1,5-cyclooctadiene)iridium shown by the following formula has been investigated. This ethylcyclopentadienyl(1,5-cyclooctadiene)iridium is a compound in which one hydrogen on the cyclopentadiene ring in cyclopentadienyl(1,5-cyclooctadiene)iridium is substituted with an ethyl group.

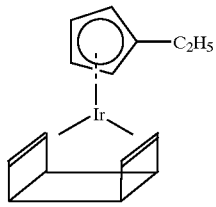

(Formula 2)

These organic precious-metal compounds have a low melting point and are liquid at room temperature, and thus are handled easily. Additionally, these compounds have a high vapor pressure, resulting in superior efficiency in manufacturing films. Therefore, these organic precious-metal compounds are considered to be eligible as CVD raw materials.

However, while the above-described bis(ethylcyclopentadienyl)ruthenium and ethylcyclopentadienyl(1,5-cyclooctadiene)iridium have superior properties as CVD raw materials, they display poor stability in the air, and in particular tend to react with oxygen, so that reaction with oxygen takes place in the air, resulting in the formation of various derivatives, such as oxides, hydroxides, and the like, as impurities. Thus, for these organic compounds, there is a problem that slight differences in the conditions during manufacturing steps tends to exert an influence on their purity and easily result in unevenness among their manufactured lots. If films are manufactured with the use of such raw materials having a purity varied from lot to lot, then it is, of course, likely that properties of the films are also varied, depending upon their raw materials.

In addition, even if manufacturing is designed so that the product is not in contact with the air at all during the manufacturing steps, it is likely that these compounds easily undergo oxidation in the course of transportation of substrates, since oxygen gas is employed as a reaction gas in order to accelerate a film-forming reaction during the manufacturing of films.

In this case, various derivatives of these compounds act as impurities, and will exert an influence on purity and electric property of the films, and what is considered as having a greater influence is morphology such as surface roughness and the like. The influence on morphology due to these impurities is on the order of nanometers, and thus seems to be extremely small as numerical values. However, in the area of DRAMs requiring densification in these days, even such small values will be responsible for whether use can be made as electrodes.

The present invention has been achieved under the background as described above, and has an object of providing an organometallic compound for chemical vapor deposition which possesses superior properties as CVD raw materials possessed by the conventional bis(ethylcyclopentadienyl) ruthenium and ethylcyclopentadienyl(1,5-cyclooctadiene) iridium and which has high stability to oxygen.

SUMMARY OF THE INVENTION

The inventors have conducted extensive research and made investigations on organometallic compounds capable of solving the above-described problems. As a result, it has been found that the following organometallic compounds with respect to ruthenium and iridium are suitable, thereby leading to the present invention.

First, there is given an explanation of organic ruthenium compounds related to the present application. A first invention related to the present application is directed to an organometallic compound for manufacturing a ruthenium film or a ruthenium compound film by a chemical vapor deposition process, wherein the organometallic compound for chemical vapor deposition is alkylcyclopentadienyl (cyclopentadienyl)ruthenium represented by the following formula:

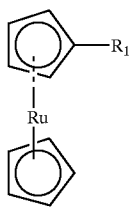

(Formula 3)

wherein the substituent $R_1$ represents any one of alkyl groups of n-propyl, iso-propyl, n-butyl, iso-butyl, and tert-butyl groups.

The organic ruthenium compounds related to the present invention have higher oxidative stability at room temperature and is not easily oxidized in the air, when compared with the conventional bis(ethylcyclopentadienyl)ruthenium. Therefore, the organic ruthenium compounds related to the present invention are not contaminated with impurities due to their partial oxidation, even if they have come in contact with the air during manufacturing and when introduced into a CVD apparatus after manufacturing. In this regard, it can be said that the organic ruthenium compounds related to the present invention are organometallic compounds allowing easier handling in manufacturing consistent films than before.

These alkylcyclopentadienyl(cyclopentadienyl) ruthenium compounds can react with oxygen and be decomposed under an atmosphere at elevated temperatures, so that these compounds will be not decomposed until they are introduced into a CVD apparatus and heated on a substrate. The rate of decomposition at high temperatures is almost the same as that of the conventional bis(ethylcyclopentadienyl) ruthenium, causing no problem in forming films.

In addition, these alkylcyclopentadienyl (cyclopentadienyl)ruthenium compounds, similarly to bis (ethylcyclopentadienyl)ruthenium, have a low melting point, resulting in easy handling, and a high vapor pressure, allowing efficient manufacturing of films, and thus are compounds having properties required as CVD raw material.

Furthermore, these alkylcyclopentadienyl (cyclopentadienyl)ruthenium compounds are synthesized with relative ease, and can be prepared by reacting bis (cyclopentadienyl)ruthenium represented by Formula 4 with an alcohol represented by Formula 5:

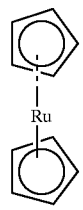

(Formula 4)

$$R_1\text{—OH} \qquad \text{(Formula 5)}$$

Wherein $R_1$ represents any one of alkyl groups of n-propyl, iso-propyl, n-butyl, iso-butyl, and tert-butyl groups.

In this reaction, it is preferable to use a catalyst, in order to promote the reaction of bis (cyclopentadienyl)ruthenium with various alcohols. As a catalyst in this case, it is preferable to employ aluminum chloride.

The following will give an explanation of organic iridium compounds related to the present application. A second invention related to the present invention is directed to an organometallic compound for manufacturing an iridium film or an iridium compound film by a chemical vapor deposition process, wherein the organometallic compound for chemical vapor deposition is alkylcyclopentadienyl(1,5-cyclooctadiene)iridium represented by the following formula:

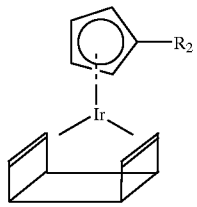

(Formula 6)

In this formula, the substituent $R_2$ in the alkylcyclopentadienyl(1,5-cyclooctadiene)iridium related to the present invention is propyl or butyl group, the propyl group including n-propyl group, iso-propyl group, and the butyl group including any one of n-butyl group, iso-butyl group, and tert-butyl group. In the present invention, these substituents are specified, since the results of inventors' investigations show that alkylcyclopentadienyl(1,5-cyclooctadiene)iridium in which an alkyl group having 5 or more carbons is introduced has an increased melting point, and thus will become unfit as CVD raw material. In case of introducing an ethyl group having two carbons, on the other hand, ethylcyclopentadienyl(1,5-cyclooctadiene)iridium as mentioned above is a substance that is already known as a raw material for iridium films, and also this prior art has poor stability to the air.

These organic iridium compounds related to the present invention also have higher stability to oxygen at room temperature and do not undergo oxidation in the air, so that there is no possibility of contamination with impurities, even if they come into contact with the air before introduced into a CVD apparatus.

In addition, the organic iridium compounds related to the present invention, similarly to the conventional ethylcyclopentadienyl(1,5-cyclooctadiene)iridium, have a low melting point and a high vapor pressure. Therefore, the organic iridium compounds related to the present invention are handled with ease and capable of efficiently manufacturing films. Thus, it can be said that these organic iridium compounds are compounds having properties required as CVD raw material.

Furthermore, these alkylcyclopentadienyl(1,5-cyclooctadiene)iridium compounds related to the present invention can be prepared with relative ease. That is, these compounds can be prepared by reacting bis(1,5-cyclooctadiene) iridium represented by the following formula with sodium alkylcyclopentadienide represented by the following formula:

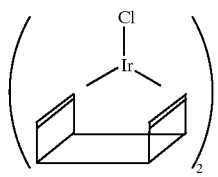

(Formula 7)

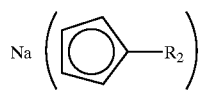

(Formula 8)

wherein the meaning of the substituent $R_2$ is as specified above.

As explained above, the organic ruthenium compounds and organic iridium compounds related to the present invention can be said to be suitable substances as raw materials for ruthenium and iridium, and compound films thereof by a CVD process. A CVD process in which these organic precious-metal compounds are applied will allow stable manufacturing of films having good morphology. In consequence, as a chemical vapor deposition process related to the present invention is utilized a chemical vapor deposition process of a precious-metal or precious-metal compound film in which these organic precious-metal compounds are vaporized, transferred onto a substrate, and decomposed by heating the substrate to laminate the precious-metal.

Regarding the substrate temperature in this case, with respect to each of compounds it is preferable that temperatures are controlled to 200° C. to 300° C. to decompose an organic precious-metal compound. Also, in this CVD step, it is preferable that the inside of a reactor is under an atmosphere at reduced pressure. Reducing the pressure in a reactor can improve the uniformity of the film-thickness distribution and step-coverage (ability to cover differences in level). The preferred range of the pressure in a reactor is 140 to 1400 Pa.

As mentioned above, any organic precious-metal compound related to the present invention has a property of easily undergoing decomposition by mixing oxygen gas into the reaction system. Therefore, in a CVD step utilizing these compounds, it is preferable that an organic precious-metal compound vaporized in an atmosphere containing oxygen gas is decomposed.

DESCRIPTION OF THE PREFERRED EMBODIMENTS

Preferable embodiments of the present invention will be described in conjunction with Comparative Examples. In this section, butylcyclopentadienyl(cyclopentadienyl) ruthenium and alkylcyclopentadienyl(1,5-cyclooctadiene) iridium related to the present invention were prepared, and ruthenium and iridium films were manufactured by a CVD process employing these organometallic compounds. Then, these films were compared with films manufactured with conventionally used raw materials.

A. Ruthenium Compounds

First Embodiment 8.0 g of bis(cyclopentadienyl)ruthenium, 3.0 g of aluminum chloride, and 80 g of polyphosphoric acid were mixed. The mixed solution was heated to 100° C. under a nitrogen atmosphere, to which 3.0 g of tert-butyl alcohol was added dropwise over 30 minutes, and then the mixture was heated to 120° C. to carry out the reaction for 4 hours. After the reaction, hot water was added to the solution to remove polyphosphoric acid, and then distillation treatment gave 2.0 g of tert-butylcyclopentadienyl(cyclopentadienyl) ruthenium. Five lots of tert-butylcyclopentadienyl (cyclopentadienyl)ruthenium were prepared by this preparing method, and subjected to film production as described later.

Comparative Example 1

For comparison with the tert-butylcyclopentadienyl (cyclopentadienyl)ruthenium prepared in the first embodiment, bis(ethylcyclopentadienyl)ruthenium was prepared. In a flask with an argon atmosphere by vacuum substitution, 200 ml of ethanol was placed, in which 25.0 g of ruthenium chloride trihydrate was dissolved, and the solution was cooled to −30° C. Then, to the solution was added 40 g of ethylcyclopentadiene, followed by 9.55 g of zinc powder (purity 99.999%, 200 meshes) in seven portions at an interval of 10 minutes. After the reaction was completed, the liquid phase was collected, from which bis(ethylcyclopentadienyl)ruthenium was extracted with hexane. As in the first embodiment, five lots of bis (ethylcyclopentadienyl)ruthenium were prepared by this preparing method, and subjected to film production. Next, ruthenium films were manufactured by a CVD process employing five lots prepared of tert-butylcyclopentadienyl (cyclopentadienyl)ruthenium and bis (ethylcyclopentadienyl)ruthenium, and examined for properties of the ruthenium films among the lots. The conditions for manufacturing the films were as follows:

Vaporization temperature: 100° C.,

Substrate temperature: 250° C.,

Reaction chamber pressure: 200 Pa,

Carrier gas/reaction gas: argon/oxygen,

Gas flow rate: 200/200 sccm.

The manufactured films were measured for the average roughness (Rms) with an AFM (atomic force microscope), whose results are shown in Table 1.

TABLE 1

| | Lot No. | | | | |
|---|---|---|---|---|---|
| | 1 | 2 | 3 | 4 | 5 |
| First Embodiment | 1.0 nm | 1.2 nm | 1.0 nm | 1.1 nm | 1.0 nm |
| Comparative Example 1 | 2.0 nm | 1.2 nm | 3.0 nm | 1.0 nm | 2.0 nm |

From these results, it has been confirmed that the ruthenium films manufactured using tert-butylcyclopentadienyl (cyclopentadienyl)ruthenium related to the first embodiment had superior roughness, regardless of the lots of the raw material. In the case of Comparative Example, bis (ethylcyclopentadienyl)ruthenium, on the other hand, the values of the surface roughness varied from lot to lot. It is believed that this is due to slight differences in the purity among the lots, because even if manufacturing have been carried out in the same steps, the time of contacting the prepared bis(ethylcyclopentadienyl)ruthenium with the air may vary delicately during the steps, or the oxygen that is the reaction gas can result in oxidation during its transportation to a substrate in manufacturing films.

Second Embodiment 8.0 g of bis(cyclopentadienyl)ruthenium, 3.0 g of aluminum chloride, and 80 g of polyphosphoric acid were mixed. The mixed solution was heated to 100° C. under a nitrogen atmosphere, to which 4.0 g of n-propyl alcohol was added dropwise over 30 minutes, and then the mixture was heated to 120° C. to carry out the reaction for 4 hours. After the reaction was completed, hot water was added to the solution to remove the polyphosphoric acid, and then distillation treatment gave 1.8 g of n-propylcyclopentadienyl (cyclopentadienyl)ruthenium.

Five lots of n-propylcyclopentadienyl(cyclopentadienyl) ruthenium were prepared in this way, and films were manufactured under the same conditions as those of the first embodiment. As a result, it has been confirmed as in the first embodiment that films can be stably manufactured which have superiority in surface roughness, regardless of the lots of the raw material.

B. Iridium Compounds

Third Embodiment

Under an atmosphere of nitrogen gas, in 350 mL of tetrahydrofuran as a solvent was dissolved 17 g of bis(1,5-cyclooctadienechloroiridium). With cooling the solution to −80° C., a solution in which 8 g of sodium n-propylcyclopentadienide was dissolved in 35 mL of tetrahydrofuran was added. The mixed solution was then reacted at −80° C. for 30 minutes, and after that the solvent was distilled off from the reaction solution, followed by hexane extraction and vacuum distillation to give 18 g of n-propylcyclopentadienyl(1,5-cyclooctadiene)iridium. Five lots of n-propylcyclopentadienyl(1,5-cyclooctadiene) iridium were prepared by this preparing method, and subjected to film production as described later.

Forth Embodiment

Using 8.5 g of sodium iso-propylcyclopentadienide instead of sodium n-propylcyclopentadienide in the third embodiment, 20 g of iso-propylcyclopentadienyl(1,5-cyclooctadiene)iridium was prepared in an otherwise similar procedure as in the second embodiment. Also, five lots of iso-propylcyclopentadienyl(1,5-cyclooctadiene)iridium were manufactured.

Fifth Embodiment

Using 8.2 g of sodium tert-butylcyclopentadienide instead of sodium n-propylcyclopentadienide in the third embodiment, 17 g of tert-butylcyclopentadienyl(1,5-cyclooctadiene)iridium was prepared in an otherwise similar procedure to that in the second embodiment. Also, five lots of tert-butylcyclopentadienyl(1,5-cyclooctadiene)iridium were prepared.

Comparative Example 2

For comparison to organic iridium compounds prepared in the above-described third to fifth embodiments, ethylcyclopentadienyl(1,5-cyclooctadiene)iridium was prepared. In this Comparative Example, using 8.5 g of sodium ethylcyclopentadienide instead of sodium n-propylcyclopentadienide in the first embodiment, ethylcyclopentadienyl(1,5-cyclooctadiene)iridium was prepared in an otherwise similar procedure to that in the second embodiment.

Next, iridium films were manufactured by a CVD process employing five lots of each of organic iridium compounds prepared in the third to fifth embodiments and in Comparative Example, and examined for properties of the iridium films among the lots. The conditions for manufacturing the films were set in the same conditions as in the film production carried out in the first embodiment.

The manufactured films were measured for the average roughness (Rms) with an AFM (atomic force microscope), whose results are shown in Table 2.

TABLE 2

|  | Lot No. | | | | |
| --- | --- | --- | --- | --- | --- |
|  | 1 | 2 | 3 | 4 | 5 |
| Third Embodiment | 1.0 nm | 1.2 nm | 1.1 nm | 1.0 nm | 1.2 nm |
| Fourth Embodiment | 0.9 nm | 1.0 nm | 1.1 nm | 0.9 nm | 1.2 nm |
| Fifth Embodiment | 1.0 nm | 1.0 nm | 1.2 nm | 1.1 nm | 1.0 nm |
| Comparative Example 2 | 2.0 nm | 1.5 nm | 1.0 nm | 0.8 nm | 2.5 nm |

From these results, it has turned out that the iridium films manufactured using the organic iridium compounds prepared in the third to fifth embodiments had superior surface roughness, regardless of the lots of the raw material. In contrast, it has been confirmed that the iridium films manufactured using the ethylcyclopentadienyl(1,5-cyclooctadiene)iridium of Comparative Example had a surface roughness varied from lot to lot, and as a result, it is difficult to stably manufacture uniform films.

What is claimed is:

1. An organometallic compound for manufacturing a ruthenium film or a ruthenium compound film by a chemical vapor deposition process, wherein the organometallic compound for chemical vapor deposition is alkylcyclopentadienyl(cyclopentadienyl)ruthenium represented by the following formula:

(Formula 1)

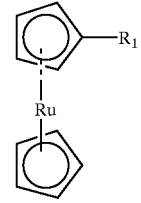

wherein the substituent $R_1$ represents any one of alkyl groups of n-propyl, iso-propyl, n-butyl, iso-butyl, and tert-butyl groups.

2. A process for preparing an organometallic compound for chemical vapor deposition according to claim 1, the process comprising reacting bis(cyclopentadienyl)ruthenium represented by Formula 2:

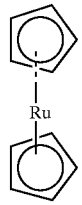

(Formula 2)

with an alcohol represented by Formula 3:

$R_1$—OH  (Formula 3)

wherein $R_1$ represents any one of alkyl groups of n-propyl, iso-propyl, n-butyl, iso-butyl, and tert-butyl groups.

3. An organometallic compound for manufacturing an iridium film or an iridium compound film by a chemical vapor deposition process, wherein the organometallic compound for chemical vapor deposition is alkylcyclopentadienyl(1,5-cyclooctadiene)iridium represented by the following formula:

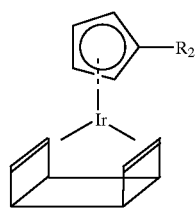

(Formula 4)

wherein the substituent $R_2$ represents any alkyl group of n-propyl, iso-propyl, or n-butyl, iso-butyl, tert-butyl group.

4. A process for preparing an organometallic compound for chemical vapor deposition according to claim 3, the process comprising reacting bis(1,5-cyclooctadienechloroiridium) having the following formula:

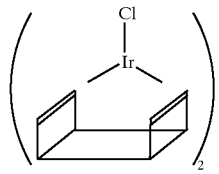

(Formula 5)

with sodium alkylcyclopentadienide having the following formula:

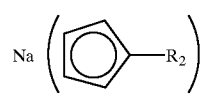

(Formula 6)

wherein the meaning of the substituent $R_2$ is as specified above.

5. A process for chemical vapor deposition of a precious-metal film or a precious-metal compound film, comprising the steps of vaporizing the organometallic compound according to claim 1 to transport it onto a substrate, and decomposing the organometallic compound by heating.

6. The process for chemical vapor deposition of a precious-metal film or a precious-metal compound film according to claim 5, wherein the organometallic compound vaporized under an atmosphere containing oxygen gas is decomposed.

* * * * *